(12) United States Patent
Clement et al.

(10) Patent No.: US 7,994,365 B2
(45) Date of Patent: Aug. 9, 2011

(54) BASIC ACETOPHENONES AS INHIBITORS OF NO-SYNTHASES

(75) Inventors: Bernd Clement, Kiel (DE); Dieter Heber, Molfsee (DE); Ullvi Bluhm, Kronshagen (DE); Uwe Buss, Kiel (DE); Friederike Friedrich-Harder, Flensburg (DE)

(73) Assignee: Christian-Albrechts-Universitaet Zu Kiel, Kiel (DE)

( * ) Notice: Subject to any disclaimer, the term of this patent is extended or adjusted under 35 U.S.C. 154(b) by 0 days.

(21) Appl. No.: 12/307,791

(22) PCT Filed: Jul. 3, 2007

(86) PCT No.: PCT/DE2007/001176
§ 371 (c)(1),
(2), (4) Date: Nov. 25, 2009

(87) PCT Pub. No.: WO2008/003299
PCT Pub. Date: Jan. 10, 2008

(65) Prior Publication Data
US 2010/0234641 A1 Sep. 16, 2010

(30) Foreign Application Priority Data
Jul. 7, 2006 (DE) .......................... 10 2006 031 813

(51) Int. Cl.
*C07C 225/16* (2006.01)

(52) U.S. Cl. ...................................................... 564/337

(58) Field of Classification Search .................. None
See application file for complete search history.

(56) References Cited

U.S. PATENT DOCUMENTS
6,743,939 B2 *   6/2004   Birkinshaw et al. .......... 558/422
2004/0176422 A1 *   9/2004   Birkinshaw et al. .......... 514/344

FOREIGN PATENT DOCUMENTS
| AU | 618 439 | 12/1991 |
| DE | 21 12 716 | 10/1972 |
| EP | 885 869 | 12/1998 |
| GB | 1 475 314 | 6/1977 |
| WO | 2004/078755 | 9/2004 |

* cited by examiner

*Primary Examiner* — Brian J Davis
(74) *Attorney, Agent, or Firm* — Diederiks & Whitelaw, PLC

(57) ABSTRACT

Use of the substance characterized by general structural formula (I)

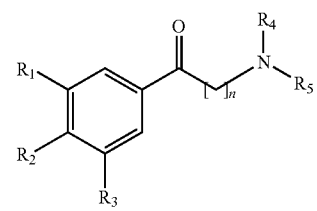

for the preparation of an agent inhibiting the enzymatic activity of NO-synthase, R1, R2, R3, R4 and/or R5 being hydrogen, an alkyl group, an aryl group or a heterocyclic group and n equals 2 or 3.

14 Claims, 1 Drawing Sheet

BASIC ACETOPHENONES AS INHIBITORS OF NO-SYNTHASES

CROSS-REFERENCE TO RELATED APPLICATIONS

This application represents a National Stage application of PCT/DE2007/001176 entitled "Basic Acetophenones as Inhibitors of No-Synthases" filed Jul. 3, 2007.

BACKGROUND OF THE INVENTION

The invention relates to basic acetophenones as inhibitors of NO-synthases and their use for producing medicaments.

NO-synthases (NOS) catalyze the reaction of the amino acid L-arginine to nitrogen monoxide (NO) and L-citrullin. Due to the participation of a surplus production of nitrogen monoxide in numerous pathophysiological processes (Stuehr., 1999, Biochim Biophys Acta, 1411, 217-230), the development of NO-synthase inhibitors is looked upon as a very promising strategy (Babu and Griffith, 1998, Curr Opin Chem Biol, 2, 491-500). A reinforcing action on the pathological processes of excessively produced nitrogen monoxide e.g. occurs with Alzheimer's disease (Dorheim et al., 1994, Biochem Biophys Res Commun, 205, 659-665), pancreatic diabetes (Li and Förstermann, 2000, J. Pathol, 190, 244-254), Parkinson's disease (Schulz et al., 1995, J. Neurochem, 64, 936-939), multiple sclerosis (Heales et al., 1999, Biochim Biophys Acta, 1410, 215-228), rheumatoid arthritis (Stefanovic-Racic et al., 1993, Arthritis Rheum, 36, 1036-1046), septicemic shock (Crossin, 1991, Trends Biochim Sci, 1991, 16, 81-82), bronchial asthma (Ligget et al., 1995, Am J Respir Crit Care Med, 152, 394-402), chronic inflammatory intestinal diseases (Boughton-Smith et al., 1993, Lancet, 342, 338-340), and migraine (Olesen et al., 1994, Trends Pharmacol Sci, 15, 149-153). Against this background over the last few years numerous inhibitors have been developed, which in part have proved effective in animal models for the indicated diseases. Particular promise is shown by the pharmacological blocking of NO-synthases of those pain processes involving an inflammatory component. In the animal model NOS inhibitors here act both on the nociceptor plane and on the transmission plane (Stegmann et al., 2001, Anasthesiol Intensivmed Notfallmed Schmerzther, 36, 276-281). Unfortunately up to now it has not been possible to develop any of said inhibitors to provide a medicament (Roman et al., 2002, Chem Rev, 102, 1179-1189).

Therefore the problem of the present invention is to provide compounds which in particular act as inhibitors for NO-synthases and which are suitable as pharmaceutical substances in medicaments.

SUMMARY OF THE INVENTION

The inventive use of the claimed substances also applies to those substances, whose R1 to R5 substituents are in each case saturated or unsaturated and/or in each case substituted or unsubstituted, where the substances can also be present as tautomers in the form of the salt or base thereof.

A characteristic example for one of the inventive substances having an inhibiting action on NO-synthase is 4'-(4-bromophenyl)-3-dimethylaminopropiophenone hydrochloride:

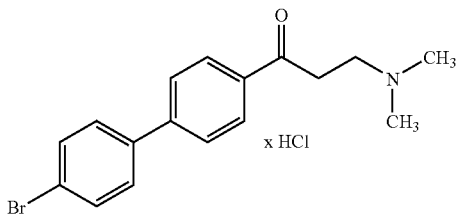

In an in vitro test system, where L-arginine is reacted in the presence of NO-synthase to L-citrullin and nitrogen monoxide (Griess assay), 4'-(4-bromophenyl)-3-dimethylaminopropiophenone hydrochloride gives rise to a concentration-dependent inhibition of up to 88% of the bNOS occurring in the central nervous system. Although the compound is known from the literature Niwa, H., 1957, Tohoku Yakka Daigaku, 4, 69-78), as yet no NOS-inhibiting action has been described.

A further example for one of the inventive substances is the compound 4'-(4-bromophenyl)-4-dimethylaminobutyrophenone hydrochloride. This substance is not known from the literature and also brings about a concentration-dependent inhibition of up to 99% of bNOS.

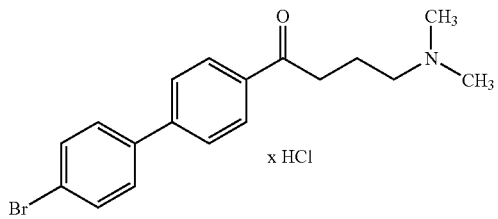

The basic acetophenones according to the invention therefore represent highly effective, low molecular weight of inhibitors of NO-synthases. They can easily and inexpensively be synthesized in high purity using standard methods. It has surprisingly been found that the inventive substances have a selectivity for the bNOS present in the central nervous system and which has been linked with neuronal diseases such as Alzheimer's disease, Parkinson's disease, multiple sclerosis and migraine. It is particularly important in this connection that the inventive inhibitors, aliphatic amines with a lipophilic group, following oral ingestion and resorption via the intestinal epithelium, are in a position to overcome the blood-brain barrier.

BRIEF DESCRIPTION OF THE DRAWINGS

The concentration-dependent activity of the inventive substances is made clearer in the following drawings, wherein show.

DETAILED DESCRIPTION OF INVENTION

Figure 1:
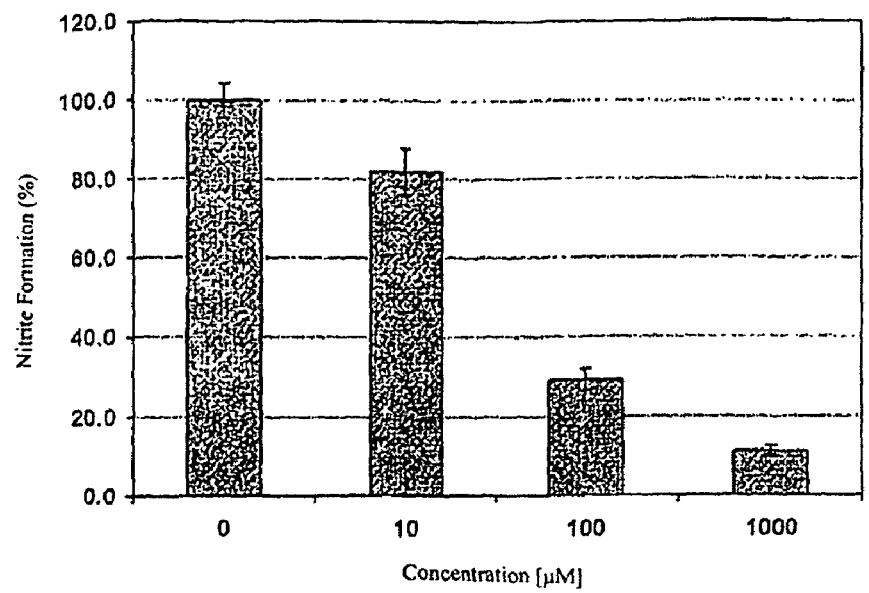
FIG. 1 The bNOS activity as a function of the 4'-(4-bromophenyl)-3-dimethylaminopropiophenone hydrochloride concentration.
Figure 2:
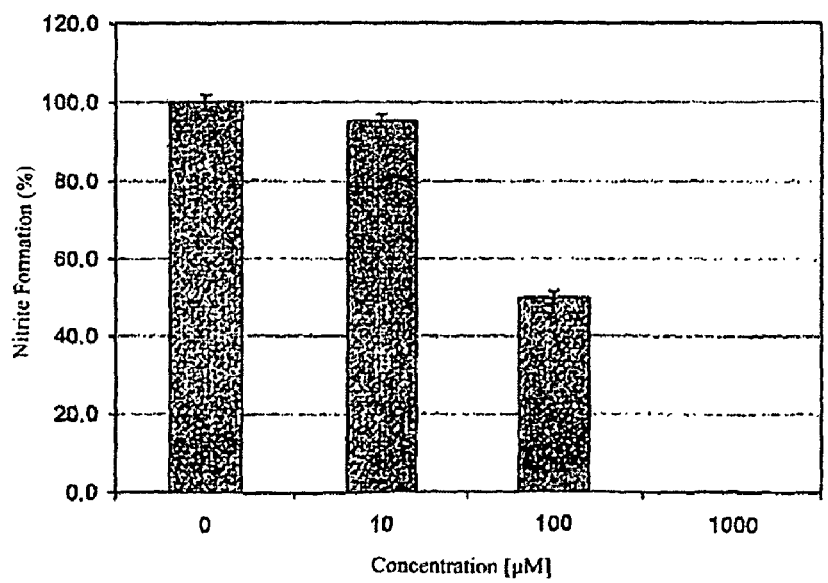
FIG. 2 The bNOS activity as a function of the 4'-(4-bromophenyl)-4-dimethylaminobutyrophenone hydrochloride concentration.

In both FIGS. 1 and 2 the bNOS activity is measured by means of nitrite formation. Nitrite is the end product of nitrogen monoxide in oxygen-containing, aqueous solution. Control incubations with all the cofactors, but without inhibitor addition, were 100% established. These are mean values +/− standard deviation of three incubations, in each case measured twice.

The synthesis of the inventive NO-synthase inhibitors and the performance of the in vitro tests in part shown in FIGS. 1 and 2 in connection with the activity thereof are explained in greater detail hereinafter.

All the inventive substances can be prepared using standard methods. Compounds with the chain length n=2 can be obtained by reacting partly substituted acetophenones with dimethyl ammonium chloride and paraformaldehyde in the sense of a Mannich reaction. To the extent that they are not commercially available, the acetophenone components were obtained by Friedel-Crafts acylations. The reaction is shown in exemplified manner hereinafter for the compound 4'-(4-bromophenyl)-3-dimethylaminopropiophenone hydrochloride:

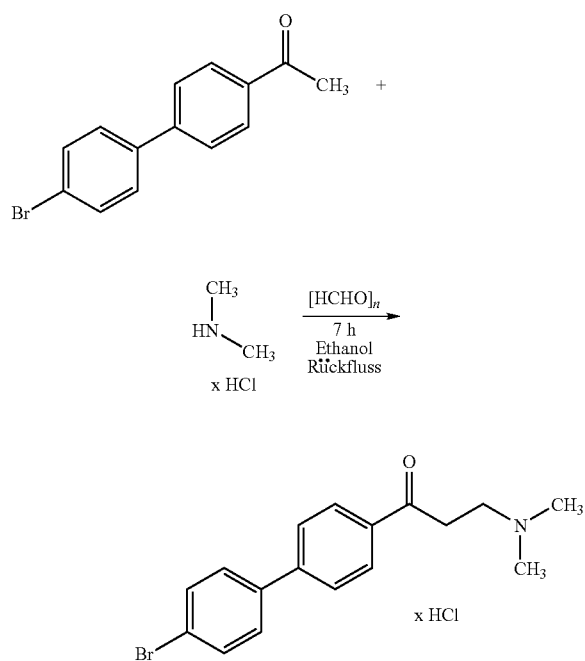

Compounds with the chain length n=3 were obtained by reacting substituted 4-chlorobutyrophenone derivatives with dimethyl amine in the sense of a nucleophilic substitution. This reaction is shown hereinafter in exemplified manner for the compound 4'-(4-bromophenyl)-4-dimethylaminobutyrophenone hydrochloride:

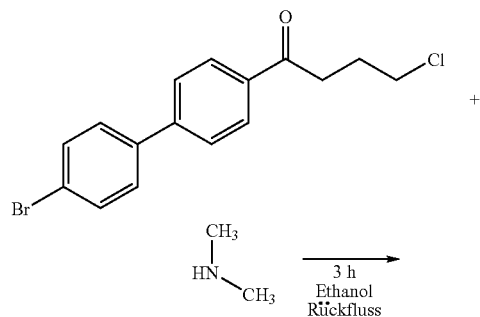

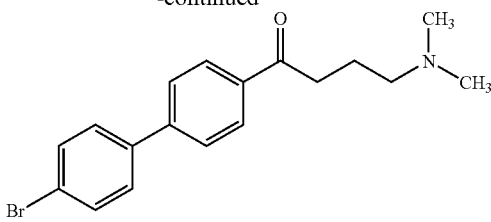

The indicated free base was subsequently precipitated as hydrochloride. The butyrophenone components, to the extent that they are not commercially available, were also obtained by Friedel-Crafts acylations.

The melting points of the synthesized substances were recorded on the Büchi 510 melting point apparatus with the Thermovar microheating stage (Reichert). NMR spectra were recorded on a Broker ARX 300 nucleoresonance spectrometer. The IR-spectra (as kBr compacts) were recorded on a Perkin-Elmer FT-IR 16 PC spectrometer. Mass spectra were recorded on a Hewlett-Packard 5989 apparatus. Elementary analyses were carried out at the Institut fur Anorganische Chemie of the CAU in Kiel using a Hekatech GmbH CHNS analyzer. Unless stated otherwise, the chemicals were obtained with maximum purity from Sigma-Aldrich GmbH. (6R)-5,6,7,8-tetrahydro-L-biopterin and the NO-synthases (bNOS, iNOS, eNOS) were obtained from Axxora GmbH. The calcium chloride, hexahydrate, dimethyl sulphoxide, ethylene diamine tetraacetic acid, naphthylene diamine dihydrochloride and nicotinamide-adenide-dinucleotide tetrasodium salt (reduced form) were obtained from Merck KGaA. Magnesium chloride hexahydrate and L-arginine were obtained from Fluka Chemie GmbH. The acetonitrile came from LGC Promochem GmbH. Calmodulin (purified, from pig brain) was obtained from Roche Diagnostics GmbH. The measurements were carried out on a Varian Cary 50 bio spectrophotometer with a water Peltier system PCB 150 and disposable microcuvettes, centre height 15 mm, volume 70-550 μl (Varian GmbH).

The incubations of the synthesized substances with the NO-synthases were carried out as follows:

The standard incubation batches have the following composition:
- 60 μl of a solution of the enzyme (in each case a recombinant human isoenzyme), the substrate and cofactors,
- 10 μl of the given incubation buffer,
- 10 μl of a solution of the potential inhibitors prepared beforehand with an 8× concentration, a partial dissolving using 10% dimethyl sulphoxide taking place, where for the control batches a further 10 μl of buffer was pipetted in place of the inhibitor solution.

Following preparation, the batches were incubated for 20 min (iNOS and eNOS) or 30 min (bNOS) in the shaking water bath at 37° C. Then, in each case 20 μl of a solution was pipetted in, which contained sodium pyruvate (1.6 mM, in the given incubation buffer) and lactate dehydrogenase (20 U/ml, in the given incubation buffer). Following a further 20 min incubation in the shaking water bath at 37° C., the incubations were stopped by adding in each case 50 μl of ice cold acetonitrile. Then any deposits were centrifuged off (uncooled laboratory centrifuge, 10,000 rpm, 5 min). In each case 120 μl of the supernatant substances were mixed with 24 μl of a solution of sulphanilamide and naphthyl ethylene diamine dihydrochloride. After incubating for 5 mM at room temperature, the solutions were measured at a wavelength of 543 nm and the indicated non-enzyme-containing sample was used as the blank reading. In the Griess assay use was made of the fact that in aqueous solutions nitrogen monoxide reacts in equimolar manner to nitrite (Ignarro et al., 1993, Proc Natl Acad Sci USA, 90, 8103-8107). The nitrite can be quantitatively determined by reaction with sulphanilamide and naphthyl ethylene diamine in an acid medium. This leads to an azo dye, which can be measured spectrophotometrically. The solution contained naphthyl ethylene diamine dihydrochloride 5.8 mM and sulphanilamide 52 mM. 1N HCl was used as the solvent. The relative nitrite formations were determined for the control batches containing no inhibitors. The following table provides a survey of all the additives and concentrations of substrate and cofactors using in the standard incubation batches. The given incubation buffer was used as the solvent. For stability reasons 0.1 mM HCl was used for tetrahydrobiopterin:

| Incubation addition | Final concentration | Storage |
| --- | --- | --- |
| L-arginine (bNOS) | 0.5 mM | 4° C. |
| L-arginine (iNOS and eNOS) | 1 mM | 4° C. |
| Tetrahydrobiopterin | 10 μM | −20° C. |
| CaCl$_2$ (bNOS and eNOS) | 0.5 mM | 4° C. |
| Calmodulin (bNOS) and eNOS) | 10 μg/ml | −20° C. |
| Flavine adenine dinucleotide, reduced form | 5 μM | −20° C. |
| Flavine mononucleotide, reduced form | 5 μM | −20° C. |
| MgCl$_2$ (iNOS) | 1 mM | 4° C. |
| Nicotinamide dinucleotide, reduced form | 0.5 mM | −20° C. |

Buffer A (incubations with bNOS):

The buffer used for bNOS incubations had the following composition: triethanolamine 50 mM, 2-mercaptoethanol 10 mM, 3-[(3-cholamidopropyl)dimethyl ammonio]-propane sulphate 1 mM, ethylene diamine tetraacetic acid 0.5 mM. The pH-value was set to 7.0 following preparation.

Buffer B (incubations with iNOS and eNOS):

Buffer B consisted of a 50 mM triethanol amine solution set at pH=7.5.

The invention claimed is:

1. A method of inhibiting enzymatic activity of NO-synthases comprising: administering a medicament including a substance with the general structural formula (I):

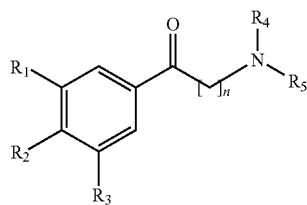

or a salt thereof, in which

R1, R3, R4 and/or R5 is hydrogen, an alkyl group, or an aryl group, and R2 is an aryl group and n is equal 2 or 3.

2. The method according to claim 1, characterized in that the substance is 4'-(4-bromophenyl)-3-dimethylaminopropiophenone, hydrochloride with structural formula (II):

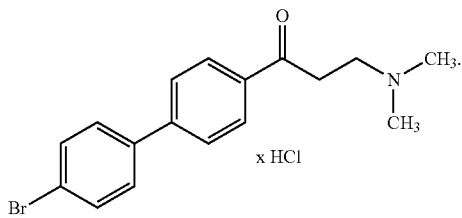

3. The method according to claim 1, characterized in that the substance is 4'-(4-bromophenyl)-4-dimethylaminobutyrophenone hydrochloride with the structural formula (III):

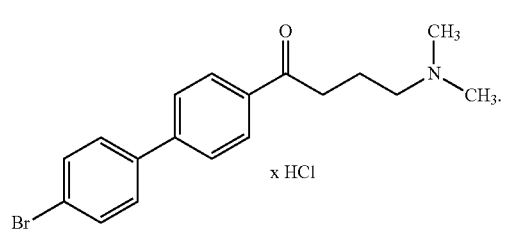

4. The method according to claim 1, characterized in that R1 and R2 and/or R2 and R3 in each case form a 4, 5, 6, 7 or 8-member ring system.

5. The method according to claim 1, characterized in that R4 and R5 in each case form a 4, 5, 6, 7 or 8-member ring system.

6. The method according to claim 2, characterized in that the substance is a tautomer of the substance with the structural formula (II).

7. The method according to claim 1, characterized in that the substance is present as a salt or a base or a tautomer of the substance with the structural formula (I).

8. The method according to claim 1, characterized in that the substance inhibits the enzymatic activity of bNOS.

9. The method according to claim 1, characterized in that the substance is used for treating Alzheimer's, pancreatic diabetes, Parkinson's, multiples sclerosis, rheumatoid arthritis, septicemic shock, bronchial asthma, chronic-inflammatory intestinal diseases or migraine.

10. The method according to claim 4, characterized in that R4 and R5 in each case form a 4, 5, 6, 7 or 8-member ring system.

11. The method according to claim 3, characterized in that the substance is a tautomer of the substance with the structural formula (III).

12. A method of treating Alzheimer's, pancreatic diabetes, Parkinson's, multiple sclerosis, rheumatoid arthritis, septicemic shock, bronchial asthma, chronic-inflammatory intestinal diseases or a migraine comprising: administering a medicament including a substance for inhibiting enzymatic activity of NO-synthases, the substance having the general structural formula (I):

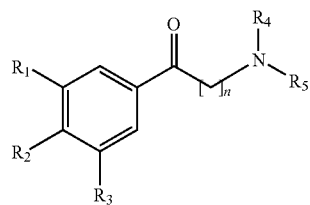

or a salt thereof, in which
R1, R3, R4 and/or R5 is hydrogen, an alkyl group, or an aryl group, and R2 is an aryl group and
n is equal to 2 or 3.

13. The method of claim 12, wherein the substance is 4'-(4-bromophenyl)-3-dimethylaminopropiophenone hydrochloride with formula (II):

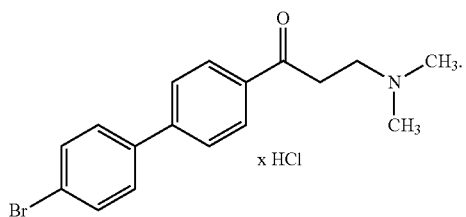

14. The method according to claim 12, wherein the substance is 4'-(4-bromophenyl)-4-dimethylaminobutyrophenone hydrochloride with the structural formula (III):

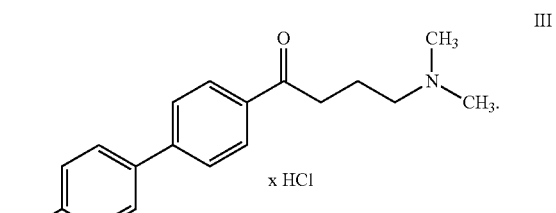

* * * * *